United States Patent [19]

Mauvernay et al.

[11] 4,105,785

[45] Aug. 8, 1978

[54] ANTI-DEPRESSIVE 2-METHYL-4-[(3'-DIMETHYLAMINO)-PROPYLIDINE]-9,10-DIHYDROBENZO[4,5]CYCLOHEPTA[1,2b]FURAN COMPOUNDS

[75] Inventors: Roland Yves Mauvernay, Riom; Norbert Busch, La Tourette; Jacques Moleyre, Menetrol, all of France

[73] Assignee: Centre Europeen de Recherches Mauvernay, Riom, France

[21] Appl. No.: 778,239

[22] Filed: Mar. 16, 1977

[30] Foreign Application Priority Data

Mar. 17, 1976 [FR] France .................... 76 07698

[51] Int. Cl.$^2$ .................. A61K 31/335; C07D 307/93
[52] U.S. Cl. ................. 424/285; 260/346.71
[58] Field of Search ............... 260/346.2 M; 424/285

[56] References Cited

U.S. PATENT DOCUMENTS

3,177,209  4/1965  Holm .................... 260/570.8 TC

FOREIGN PATENT DOCUMENTS

1,225,660  9/1966  Fed. Rep. of Germany.

OTHER PUBLICATIONS

Rivalle et al., Tetrahedron, vol. 32, pp. 829–834, Apr. 1976.

*Primary Examiner*—Henry R. Jiles
*Assistant Examiner*—Bernard Dentz
*Attorney, Agent, or Firm*—Haseltine, Lake & Waters

[57] ABSTRACT

Substituted methyl-2-[(dimethylamino-3')propylidene]-4-dihydro-9,10-benzo-[4,5]cyclohepta[1,2-b]-furan compounds are described which are useful in the treatment of depressive syndromes and which may be obtained by cyclization from substituted derivatives of furan.

3 Claims, No Drawings

ANTI-DEPRESSIVE 2-METHYL-4-[(3'-DIMETHYLAMINO)-PROPYLIDINE]-9,10-DIHYDROBENZO [4,5]CYCLOHEPTA[1,2b]FURAN COMPOUNDS

The present invention relates to new tricyclic compounds comprising a furan ring, or substituted methyl-2-[(dimethylamino-3') propylidene]-4 dihydro-9,10 benzo-[4,5] cyclohepta [1,2-b] furan compounds.

It also relates to a process for obtaining these compounds by cyclization from substituted furan derivatives and the application thereof in therapy as thymoanaleptic medicines. The medicines used in psychotherapy are of recent origin and, since the discovery of the neuroleptic properties of chlorpromazine, research on phenothiazine derivatives has made it possible to discover substances which are of the utmost importance in therapy. These successes led to research workers studying other tricyclic structures, and particularly iminodibenzyl derivatives and their homologues, which constitute the larger of the two families of thymoanaleptics, the second of these two families consisting of M.A.O.Is (monoamine-oxidase inhibitors).

Among all the compounds discovered up to the present, the following may be mentioned as being the most representative of two sub-groups: imipramine (imipraminic sub-group) and amitriptyline (dibenzocycloheptadienes sub-group).

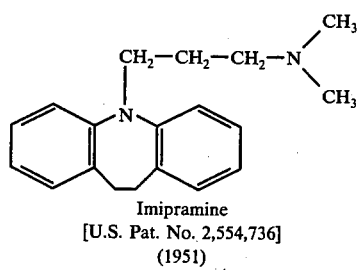

Imipramine
[U.S. Pat. No. 2,554,736]
(1951)

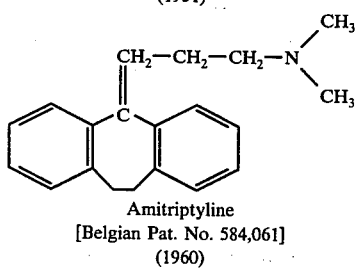

Amitriptyline
[Belgian Pat. No. 584,061]
(1960)

It has now, surprisingly, been found that new compounds, which have a general dibenzocycloheptadiene structure, but wherein a phenyl ring is replaced by a furyl ring, possess interesting thymoanaleptic properties, as will be seen from the report of pharmalogical trials given hereinbelow.

A first object of the present invention therefore consists of the compounds having the following general formula:

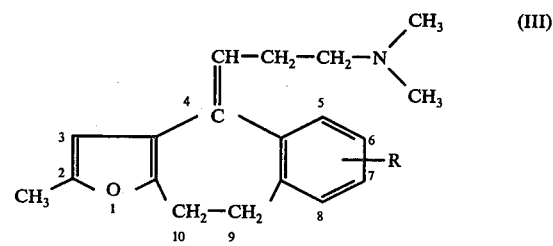

wherein R is hydrogen or a lower alkyl radical.

The process of the invention for producing compounds of formula III comprises the five series of reactions consisting in:

(1) treating bromomethyl-2-carbethoxy-3 furan in a known manner, with triethylphosphite and then reacting the phosphonate obtained with sodium hydride at a low temperature and in a solvent medium, and subsequently with a benzoic aldehyde suitably substituted with a radical R which is hydrogen or a lower alkyl radical, and subjecting the ethylenic compound obtained to catalytic hydrogenation under pressure;

(2) preparing, in a known manner, the formylated compound in position 5 of the furan ring of the substituted phenethyl-2 carbethoxy-3 furan obtained in (1) and treating the aldehyde ester so obtained, first with semicarbazide hydrochloride with reflux heating in an alcohol solution and then with potassium hydroxide;

(3) reacting a benzene solution of the phenethyl-2 methyl-5 furan carboxylic-3 acid obtained in (2) with phosphorus pentachloride;

(4) by means of aluminium chloride, effecting the cyclization of the acid chloride obtained in (3) and putting the resulting compound into solution in anhydrous dichloromethane; and (5) using dimethylamino-propane magnesium iodide to effect a Grignard reaction on the 4H-dihydro-9,10 benzo [4,5] cyclohepta [1,2-b] furanone-4 obtained in (4), then hydrolyzing and dehydrating the product of the said Grignard reaction.

This process therefore comprises 5 reaction steps, a preferred form of embodiment of which is given hereinafter.

In the first step, substituted phenethyl-2 carbethoxy-3 furan compounds are prepared.

For this, the starting disubstituted furan (IV) is treated with triethylphosphite, by the method described by U. Michael and S. Gronowitz [Chemica Scripta 4, 126 (1973)], then the phosphonate obtained is treated with sodium hydride at low temperature and using a solvent such as dimethoxy-1,2 ethane (DME) and then with a benzoic aldehyde substituted with the radical R as defined hereinabove.

Finally, the ethylenic compound obtained is subjected to catalytic hydrogenation under pressure, the catalyst used preferably being 30% palladinized charcoal.

This first series of reactions corresponds to the following reactions sequence:

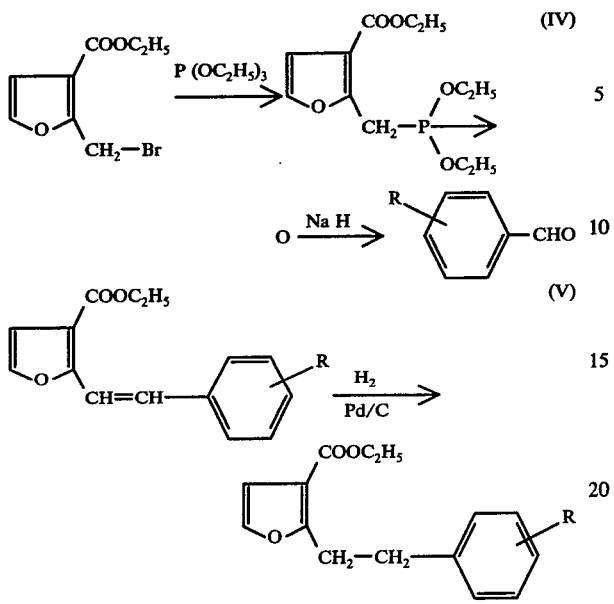

In the second step, phenethyl-2-methyl-5 furan carboxylic-3 acids are prepared. For this, and starting with the compound obtained in the previous step, the compound formylated in position 5 on the furan ring is first prepared by the method described by J. P. Marquet et al. [Bull. Soc. Chim. 2323 (1973)], and the aldehyde ester thus obtained is treated, first with semicarbazide hydrochloride, the mixture being reflux-heated in an ethanol solution, then with potassium hydroxide. This second series of reactions corresponds to the following reaction sequence:

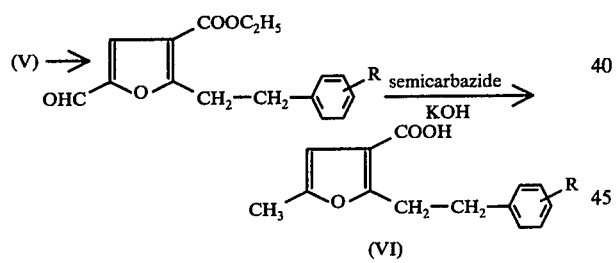

In the third step, chlorides of the acids obtained in the preceeding step are prepared.

For this, phosphorus pentachloride is reacted with a benzene solution of an acid (VI).

The following is the reaction sequence:

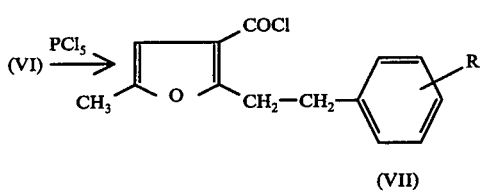

In the fourth step, cyclization of the compounds obtained in the previous step is effected to obtain 4H-dihydro-9,10-benzo [4,5]cyclohepta [1,2-b] furanones-4.

For this, aluminium chloride is used as the cyclization catalyst which is caused to react on compound (VII) in solution in anhydrous dichloromethane, the temperature being maintained at about 0° C as the reaction begins.

The reaction sequence is as follows:

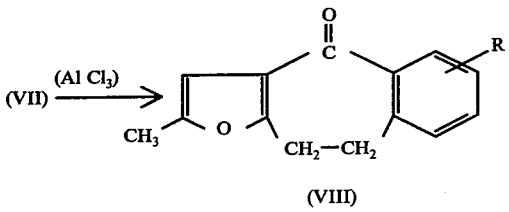

In the fifth step, a compound according to the invention is prepared from a furanone (VIII).

For this, a Grignard reaction is effected on the furanone (VIII) with dimethylamino propyl magnesium iodide, followed by hydrolysis and dehydration with acetic anhydride.

The reaction sequence is as follows:

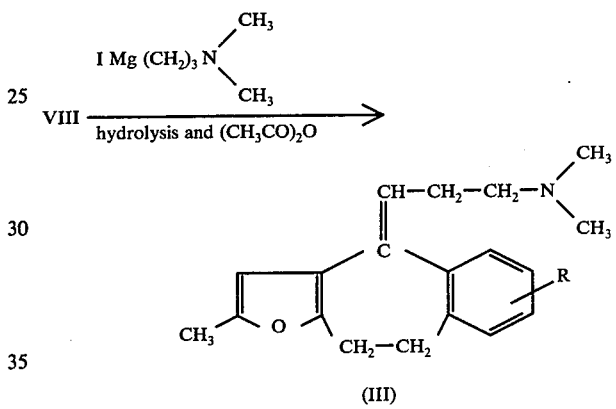

The invention is described in greater detail in the following examples, which in no way limit it and relate to the synthesis of dimethyl-2,7 [(dimethylamino-3') propylidene]-4 dihydro-9,10 benzo-[4,5] cyclohepta [1,2-b] furan (compound no. 1).

EXAMPLE 1

First step: [(methyl-3') phenethyl]-2 ethoxycarbonyl-3 furan

An equimolar mixture of bromomethyl-2 ethoxycarbonyl-3 furan (232 g) and triethylphosphite (166 g) was heated progressively until the start of the reaction, then at 150° C for 3 hours. After distillation, 239 g of (ethoxycarbonyl-3 furylmethyl-2)-diethyl phosphonate with a boiling point $BP_{20} = 205°-210°$ C was obtained.

To a dispersion of 4.8 g (0.1 M) sodium hydride at 50% in oil, in 100 ml dimethoxy-1,2 ethane (DME), 29 g (0.1 M) of the phosphonate previously obtained, in solution in 100 ml of DME, was added dropwise and with adequate stirring; when hydrogen no longer evolved, 12 g (0.1 M) meta-tolylaldehyde was added dropwise; at the end of the reaction the reaction mixture was poured into 1 liter of water, ether-extraction was effected several times and, after the ether had been stripped at low pressure, fractional distillation of the residual oil was effected; the olefin obtained had a boiling point $BP_{12} = 202°-212°$ C.

To hydrogenate said olefin, 25 g of it were dissolved in 300 ml ethanol, 0.2 g of 30% palladinized charcoal was added and the mixture was introduced into an autoclave into which hydrogen was admitted at a pressure of 40 bars. The mixture was stirred until the theoretical amount of hydrogen had been absorbed. After filtration of the catalyst and evaporation of ethanol, an oil was obtained which, after fractional distillation, had a boiling point $BP_{10} = 182°-184°$ C.

Second step: [(methyl-3')phenethyl]-2-methyl-5-furan carboxylic-3 acid 25.5 g of the compound obtained in the preceeding step was treated with the dimethylformamide-phosphorus oxychloride complex (DMF: 7 g; $POCl_3$: 18 g), the phosphorus oxichloride being added progressively, the mixture then being heated in a water bath for 3 hours.

The reaction mixture was then poured into 300 ml of a saturated sodium acetate solution, chloroform extraction then being effected; after evaporation of the solvent and distillation the aldehyde ester having a boiling point $BP_{15} = 220°$ C was obtained.

28 g of the aldehyde ester obtained previously was then dissolved in 200 ml ethanol; 11 g of semicarbazide hydrochloride and 15 g hydrated sodium acetate was added; after reflux heating the mixture for 1 hour the ethanol was stripped, the solid product obtained was washed with hot water, it was dried and the intermediate semi-carbazone thus obtained was used directly for the following reaction, by introducing 16.8 g of sodium hydroxide dissolved in 250 ml of diethylene glycol.

The reaction mixture was reflux heated for 3 hours and then concentrated to one third of its volume under low pressure; the residue was dissolved in cold water and then acidified with normal hydrochloric acid. The furan carboxylic acid obtained was vacuum-dried and recrystallized in ethanol, thus obtaining colourless needles or microcrystals having a melting point $MP = 118°-120°$ C.

Third step: [(methyl-3')phenethyl]2 methyl-5 furan carboxylic-3 acid chloride 24.4 g (0.1 M) of the acid obtained in the preceeding step and 21 g (0.1 M) phosphorus pentachloride were put into 200 ml benzene. The mixture was stirred for 4 hours, the benzene and oxychloride formed were stripped by evaporation in a water bath under low pressure, thus obtaining a residual oil corresponding to the acid chloride desired, which was used directly in this form in the following step.

Fourth step: 4H-dimethyl-2,7 dihydro-9,10 benzo [4,5] cyclohepta [1,2-b] furanone-4.

13.5 g of aluminium chloride was added at one time to a solution of 26 g (# 0.1 M) of the acid chloride prepared in the previous step in 250 ml of anhydrous dichloromethane, and the mixture was maintained with stirring at 0° C for 2 hours and then at ambient temperature for 1 hour.

The mixture was then poured into 250 ml of normal hydrochloric acid; after stirring for 2 hours at ambient temperature and extraction of the aqueous phase with methylene chloride, the whole of the organic phase was washed with water and then extracted with a sodium bicarbonate solution and then again washed with water. Drying on sodium sulphate, followed by evaporation of the solvent under low pressure, provided a residue which was then subjected to fractional distillation. The compound obtained has a boiling point $BP_{15} = 208°-212°$ C.

Fifth step: Dimethyl-2,7 [(dimethylamino-3')-propylidene]-4 dihydro-9,10 benzo-[4,5] cyclohepta-[1,2-b] furan.

The iodide derivative of dimethylamino propane magnesium was first prepared in situ; for this, 1.82 g magnesium and an iodine crystal were introduced into a reactor and heated until the iodine was sublimated and, after cooling, 10 ml of anhydrous tetrahydrofuran (dry THF) was added, the mixture was heated to boiling and a solution of 0.4 g ethyliodide in 10 ml dry THF was added dropwise.

After the start of the reaction a solution of 9.1 g dimethylamino-3 chloro-1 propane in 30 ml THF was added. After all the magnesium had disappeared, the mixture was cooled and a solution of 11.3 g of the compound prepared in the previous step was added dropwise. The reaction was left to continue for 20 hours at ambient temperature and the solution was poured into 300 ml of sodium chloride saturated water. After extraction with ether, the product was washed with sodium chloride saturated water and then dried, the solvent being then stripped.

The oily residue obtained was then dehydrated by treating it with boiling acetic anhydride. The excess anhydride and acetic acid formed were removed and 100 ml of 0.5 N hydrochloric acid was added and the product was subjected to extraction with benzene. Following an alkalinization of the hydrochloric phase, an oil was precipitated which was treated with chloroform, washed with water and dried on anhydrous sodium sulphate. After removal of the solvent and distillation, the compound of the title was obtained in the form of a viscous oil with a boiling point $BP_1 = 178°-183°$ C and having the following elementary analysis:

|  | C % | H % | N % |
|---|---|---|---|
| Calculated | 81.31 | 8.53 | 4.74 |
| Found | 80.19 | 8.33 | 4.85 |

EXAMPLE 2

By repeating the same series of reactions under the same conditions as in example 1, but using paratolylaldehyde as the aldehyde in the first step, dimethyl-2,6 [(dimethylamino-3')]-propylidene -4 dihydro-9,10 benzo [4,5] cyclohepta [1,2-b] furan (compound no. 2) was obtained in the form of a very viscous oil having a boiling point $BP_{0.5} = 165°$ C and the following elementary analysis:

|  | C % | H % | N % |
|---|---|---|---|
| Calculated | 81.31 | 8.53 | 4.74 |
| Found | 80.74 | 8.56 | 4.92 |

EXAMPLE 3

By operating as explained in example 1, but using benzaldehyde as the aldehyde in the first step, methyl-2 [(dimethylamino-3')-propylidene]-4 dihydro-9,10 benzo-[4,5] cyclohepta [1,2-b] furan was obtained in the form of a yellow oil having a boiling point $BP_{0.4} = 159°$ C and giving the following elementary analysis:

|  | C % | H % | N % |
|---|---|---|---|
| Calculated | 81.10 | 8.24 | 4.98 |
| Found | 80.99 | 8.29 | 4.70 |

PHARMACOLOGICAL DATA

The psychopharmacological properties of the compounds of the invention, which allow them to be used in therapeutics, have been evaluated by a series of tests the most significant results of which are given below, compared with those obtained with amitriptyline. The test proceedings are given with reference to the authors who described them for the first time, and the experimental values obtained are given in table I.

(1) Acute toxicity by the oral way in the mouse

This was evaluated in the mouse by the method of Behrens and Karber [Arch. Exp. Path. Pharm. 177, 379 (1935)]

(2) Antagonism to reserpine-induced hypothermia

Administration of reserpine to the mouse (1 mg/kg IV) results in hypothermia which may be antagonized by certain anti-depressants.

The values given in table I correspond, for the doses given, to the maximal rise in temperature. [Boissier et al., Thérapie 1966, XXI, 109-117]

(3) Antagonism to catalepsy induced by prochlorperazine in the rat.

Injection of prochlorperazine in the rat induces a cataleptic state which is more or less inhibited by antidepressants. The values given in table I show percentages of inhibition. [Boissier J. R. and Simon P., Thérapie (1963), 18, 1257-77]

(4) Potentialization of stereotypies induced by amphetamine in the rat.

The administration of D-amphetamine to the rat (4 mg/kg IP) results in stereotyped behaviour which can be potentialized or antagonized by various products.

The values given in table I show the percentage of potentialization. [Lapin I. P. and Schelkunov E. L. (1963) Second International Pharmacological Meeting 1, 205 Pergamon Press].

(5) Antioxotremoric action in the mouse

The administration of oxotremorine to the mouse (2 mg/kg IP) induces symptoms of trembling.

The values given in table I show the percentages of inhibition of these symptoms. [Everett G. M., Nature, London 177, 1238 (1956)]

(6) Spontaneous motility in the mouse

One hour after the administration of the product to be studied, the animals are placed by groups of two in a circular corridor swept by beams of infrared light making it possible to count their movements from one place to another. The number of movements from one place to another is counted for 10 minutes and compared with the score obtained by a control group.

Table I shows the percentage of decrease in the number of movements for doses given.

(7) Analgesic activity

This was assessed on the mouse by the hot plate method.

The values given in table I show the dose in mg/kg PO (i.e. orally) of the product of the invention which enables 50% of the animals treated to remain exposed to heat stimulus for longer than 5 seconds. [Eddy N. B. and Leimbach D. J., Pharmacol. Exp. Ther., 107, 385-393 (1953)]

Conventional psychopharmacological tests show that the compounds of the invention possess antidepressant properties (anti-reserpine and anti-cataleptic actions); the significant action of compound no. 3 on reserpine-induced hypothermy should particularly be noted.

The test of stereotypies to amphetamine shows that the compounds of the invention have no neuroleptic component. All the compounds of the invention have moderate central anticholinergic action, resulting in a substantial lowering of spontaneous motility in the mouse, and certain of them have an additional analgesic activity. It is therefore possible to use the compounds of the invention, and especially compound no. 3, in therapy for the treatment of depressive syndromes at daily doses which may lie in the range of 50 to 250 mg according to the method of administration.

TABLE I

| TESTS | compound no. 1 | | compound no. 2 | | compound no. 3 | | AMITRIPTYLINE | |
|---|---|---|---|---|---|---|---|---|
| | doses x mg/kg | Results | doses x mg/kg | Results | doses x mg/kg | Results | doses x mg/kg | Results |
| [1]acute toxicity | 600 PO | 1 death/10 | 600 PO | 1 death/10 | LD/50 | 300 mg/kg PO | LD 50 | 250 mg/kg PO |
| HYPOTHERMIA (Reserpine) | 12.5 PO | +1° C | 25 PO | +0.6° C | 50 PO | +3° C | 50 PO | +2.5° C |
| [3]CATALEPSY (Prochlorperazine) | 20 IP | −26.1% | 20 IP | −44.4% | 40 IP | −33.3% | 20 IP | −33,3% |
| [4]STEREOTYPIES (Amphetamine) | 5 IP | +105% | 5 IP | +141% | 5 IP | +9,2% | 20 PO | +65% |
| [5]ANTI-OXOTREMORIC ACTION | 100 PO | −35% | 100 PO | −30% | 100 PO | −75% | 100 PO | −100% |
| SPONTANEOUS MOTILITY | 100 PO | −95.3% | 100 PO | −84.4% | 100 PO | −84% | 80 PO | −80% |
| ANALGESIA | ED 50 | 48 mg/kg PO | ED 50 | 47 mg/kg PO | non specific action | | ED 50 | 16 mg/kg PO | x Method of administration : PO = per os; IP = intraperitoneal way

What is claimed is:

1. Tricyclic compounds comprising a furan ring, which correspond to the formula:

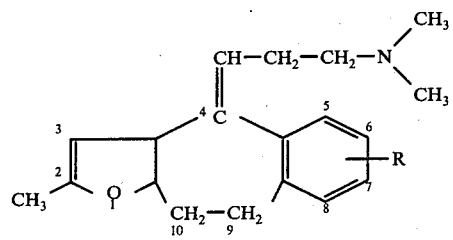

wherein R is hydrogen or a lower alkyl radical.

2. A compound according to claim 1, which is selected from the group consisting of:
dimethyl-2,7 [(dimethylamino-3′) propylidene]-4 dihydro-9,10 benzo-[4,5] cyclohepta [1,2-b] furan, dimethyl-2,6 [(dimethylamino-3′) propylidene]-4 dihydro-9,10 benzo-[4,5] cyclohepta [1,2-b] furan, and methyl-2 [(dimethylamino-3′) propylidene]-4 dihydro-9,10 benzo-[4,5] cyclohepta [1,2-b] furan.

3. A method of treatment of depressive syndromes which comprises administering to a host in need thereof a therapeutically effective amount of a compound of claim 1.

* * * * *